(12) United States Patent
Slupchynskyj

(10) Patent No.: US 10,028,762 B1
(45) Date of Patent: Jul. 24, 2018

(54) METHOD OF CUTTING SOFT TISSUE UNDER FACIAL SKIN

(71) Applicant: Percutaneous Cosmetic Devices, LLC, Wilmington, DE (US)

(72) Inventor: Oleh Slupchynskyj, Chatham, NJ (US)

(73) Assignee: Percutaneous Cosmetic Devices LLC, Wilmington, DE (US)

( * ) Notice: Subject to any disclaimer, the term of this patent is extended or adjusted under 35 U.S.C. 154(b) by 507 days.

(21) Appl. No.: 14/264,015

(22) Filed: Apr. 28, 2014

Related U.S. Application Data

(60) Provisional application No. 61/890,640, filed on Oct. 14, 2013.

(51) Int. Cl.
*A61B 17/32* (2006.01)
*A61B 17/00* (2006.01)

(52) U.S. Cl.
CPC ........ *A61B 17/32002* (2013.01); *A61B 17/00* (2013.01); *A61B 2017/00792* (2013.01)

(58) Field of Classification Search
CPC ..... A61B 17/3002; A61B 17/32; A61B 17/34; A61B 10/0233
USPC ................................. 606/170–171
See application file for complete search history.

(56) References Cited

U.S. PATENT DOCUMENTS

| | | | |
|---|---|---|---|
| 5,403,276 A * | 4/1995 | Schechter | A61B 17/32002 604/118 |
| 5,467,763 A | 11/1995 | McMahon | |
| 5,840,044 A | 11/1998 | Dassa | |
| 6,306,135 B1 * | 10/2001 | Ellman | A61B 18/1477 606/45 |
| 7,896,879 B2 | 3/2011 | Solsberg | |
| 8,343,179 B2 | 1/2013 | To | |
| 2005/0055073 A1 * | 3/2005 | Weber | A61B 18/1402 607/99 |
| 2006/0094983 A1 | 5/2006 | Burbank | |
| 2006/0224083 A1 | 10/2006 | Clifford | |
| 2006/0241673 A1 * | 10/2006 | Zadini | A61B 17/0218 606/192 |
| 2007/0255303 A1 | 11/2007 | Bakos | |
| 2008/0109023 A1 * | 5/2008 | Greer | A61B 17/320016 606/170 |
| 2008/0114364 A1 | 5/2008 | Goldin | |
| 2008/0249552 A1 | 10/2008 | Eliachar | |
| 2010/0036312 A1 * | 2/2010 | Krolik | A61B 17/221 604/22 |
| 2011/0245727 A1 | 10/2011 | Flatland | |

(Continued)

*Primary Examiner* — Christopher L Templeton
*Assistant Examiner* — George J Ulsh
(74) *Attorney, Agent, or Firm* — PK Patent Law

(57) ABSTRACT

The NEEDLE KNIFE APPARATUSES, METHODS AND SYSTEMS ("NK") may have a cannula, through which a needle knife may be deployed. The needle knife may oscillate to cut through a patient's tissue, such as muscle tissue in the forehead of a patient to eliminate forehead wrinkles. In certain embodiments, the knife portion of the needle knife is normally sheathed within a cannula during insertion into and removal from a patient. The oscillation may be performed manually or by a motor, which may be attached via a connection mechanism. The connection mechanism may include a colley system or be glued in place. Once inserted into a patient, the oscillating motor mechanism is engaged to rapidly oscillate the needle knife to expose the knife to rapidly cut soft tissue.

13 Claims, 25 Drawing Sheets

(56) References Cited

U.S. PATENT DOCUMENTS

2012/0277674 A1 11/2012 Clark
2013/0197550 A1* 8/2013 Dietz ............. A61B 17/320068
606/169

* cited by examiner

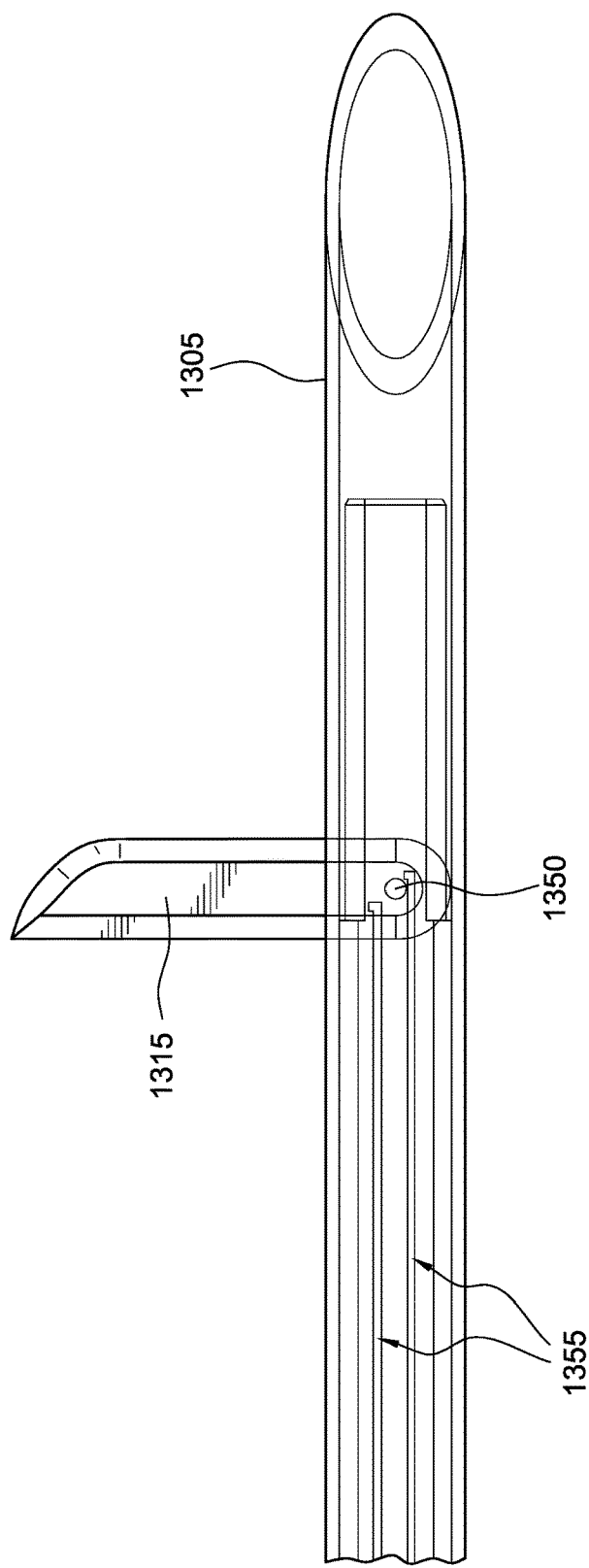

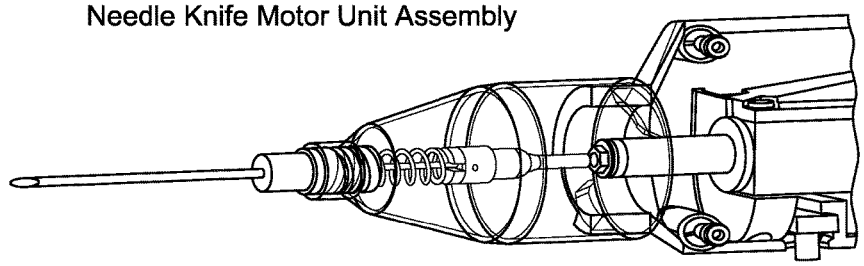
FIG. 17g
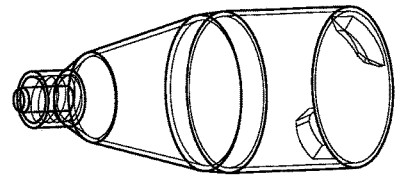
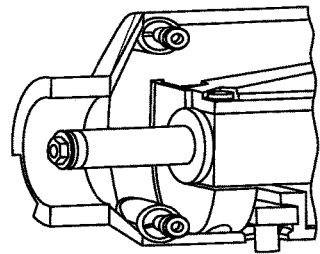
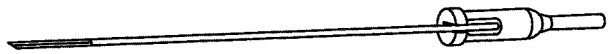
 
FIG. 17h

METHOD OF CUTTING SOFT TISSUE UNDER FACIAL SKIN

PRIORITY CLAIM

Applicant hereby claims benefit to priority under 35 USC § 119 as a non-provisional conversion of U.S. provisional patent application Ser. No. 61/890,640, filed Oct. 14, 2013, entitled "Needle Knife Apparatuses, Methods and Systems."

This application for letters patent disclosure document describes inventive aspects that include various novel innovations (hereinafter "disclosure") and contains material that is subject to copyright, mask work, and/or other intellectual property protection. The respective owners of such intellectual property have no objection to the facsimile reproduction of the disclosure by anyone as it appears in published Patent Office file/records, but otherwise reserve all rights.

The entire contents of the aforementioned application is herein expressly incorporated by reference.

FIELD

The present innovations generally address medical devices, needles, and medical-grade blades and more particularly, include NEEDLE KNIFE APPARATUSES, METHODS AND SYSTEMS.

However, in order to develop a reader's understanding of the innovations, disclosures have been compiled into a single description to illustrate and clarify how aspects of these innovations operate independently, interoperate as between individual innovations, and/or cooperate collectively. The application goes on to further describe the interrelations and synergies as between the various innovations; all of which is to further compliance with 35 U.S.C. § 112.

BACKGROUND

Small medical devices and small surgical blades may be used for various medical procedures. Various methods also exist for removing wrinkles from a person's body, and in particular, their face and forehead, such as face lifts and injecting Botox.

BRIEF DESCRIPTION OF THE DRAWINGS

The accompanying appendices and/or drawings illustrate various non-limiting, example, innovative aspects in accordance with the present descriptions:

FIG. 13 shows a diagram illustrating further embodiments of the NK.

FIG. 14*c* shows the blade in an oscillating cutting position.

FIGS. 17*a-h* shows various diagrams illustrating a series of exploded and assembled views of yet another embodiment of the NK.

The leading number of each reference number within the drawings indicates the figure in which that reference number is introduced and/or detailed. As such, a detailed discussion of reference number 101 would be found and/or introduced in FIG. 1. Reference number 201 is introduced in FIG. 2, etc.

DETAILED DESCRIPTION

Introduction

In one implementation, a minimally invasive needle knife is used for permanent glabellar and crows feet wrinkle reduction. The device consists of a needle which is inserted into the areas of the forehead and facial skin that cause glabellar frown lines and crows feet. Once the needle is inserted, a small knife within the needle lumen is activated and the muscles and nerves responsible for wrinkle creation are severed. This creates a permanent elimination in the wrinkle in that area.

In one implementation, a surgical-grade blade may disposed along a needle disposed within a lumen or cannula assembly. The needle may be inserted into a patient, and the blade may then be deployed to perform various procedures. In some embodiments, an 18 gauge needle may be used. In other embodiments, a 16 gauge needle may be used.

In some embodiments, the needle may be inserted into the forehead of a patient to cut the patient's muscles in their forehead, thereby permanently removing wrinkles. This may avoid any potential dangers associated with the use of Botox and other similar such methods.

NK

Figure 1:
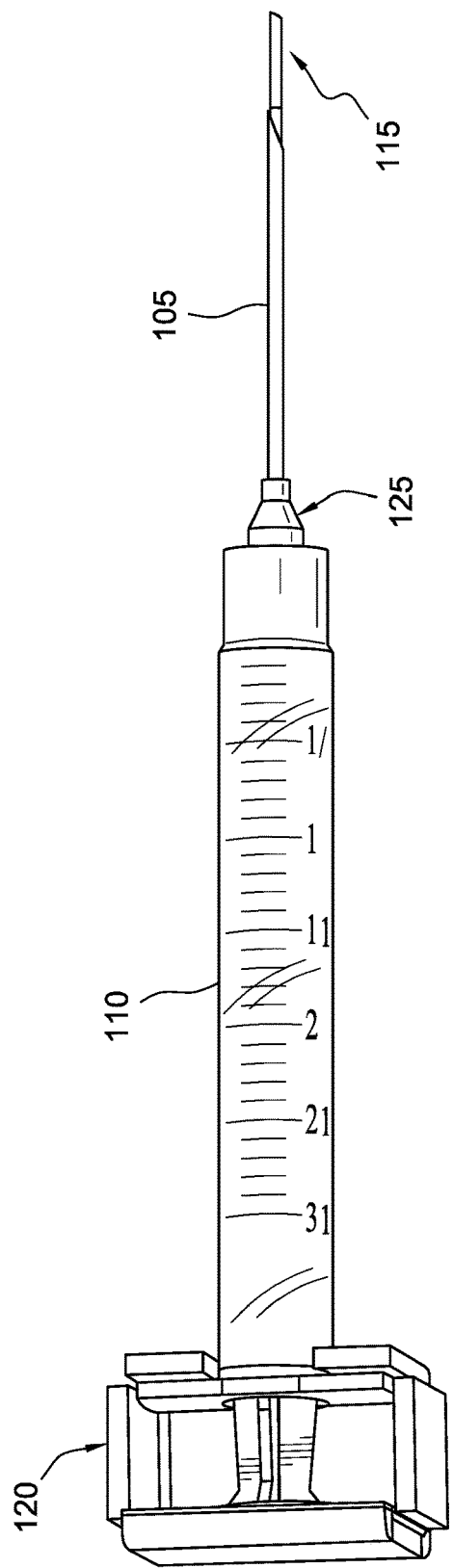
FIG. 1 shows a diagram illustrating an embodiment of the Needle Knife (hereinafter "NK")

FIG. 1 illustrates an embodiment of the NK. In one embodiment, the needle 105, shown here attached to a syringe 110, may contain a blade 115. The needle 105 may be inserted under the skin of a patient. The blade 115 may deploy after insertion, and may then be used to perform various medical functions. In one implementation, the blade 115 may be deployed to cut muscles in the forehead of a patient, thereby permanently eliminating forehead wrinkles.

The syringe 110 may be attached, via a connector mechanism 125, to a control mechanism 120. In some embodiments, the control mechanism may control deployment of the blade. The control mechanism may also control the speed at which the blade moves once it is inserted into the patient. In some embodiments, the doctor may control the deployment and/or motion of the blade by hand. In alternative embodiments, the deployment and/or motion of the blade may be controlled by a computerized and/or automated device.

In one implementation, the control mechanism may also have a safety mechanism. The safety mechanism may, in some embodiments, detect if the blade hits bone or other unintended types of tissue. If the safety mechanism hits the other types of tissue, such as bone, the safety mechanism may engage and stop the motion of the blade. In some implementations, the safety mechanism may have an alert system to notify the doctor using the NK that (s)he has hit unintended matter, and, in a further embodiment, may be able to notify the doctor of what type of matter hit, for example, by detecting the density of the matter hit. In certain other embodiments, the NK is configured to shave bone and cut cartilage. As such, the device may be configured to notify the doctor that the NK has hit bone or cartilage to potentially adjust the speed at which the device operates, so as to facilitate the cutting of the bone or cartilage.

In another embodiment, ultrasound or other imaging techniques may be used to track the location of the needle and/or blade. In such embodiments, ultrasound or other markings may be incorporated into the needle.

Figure 2:
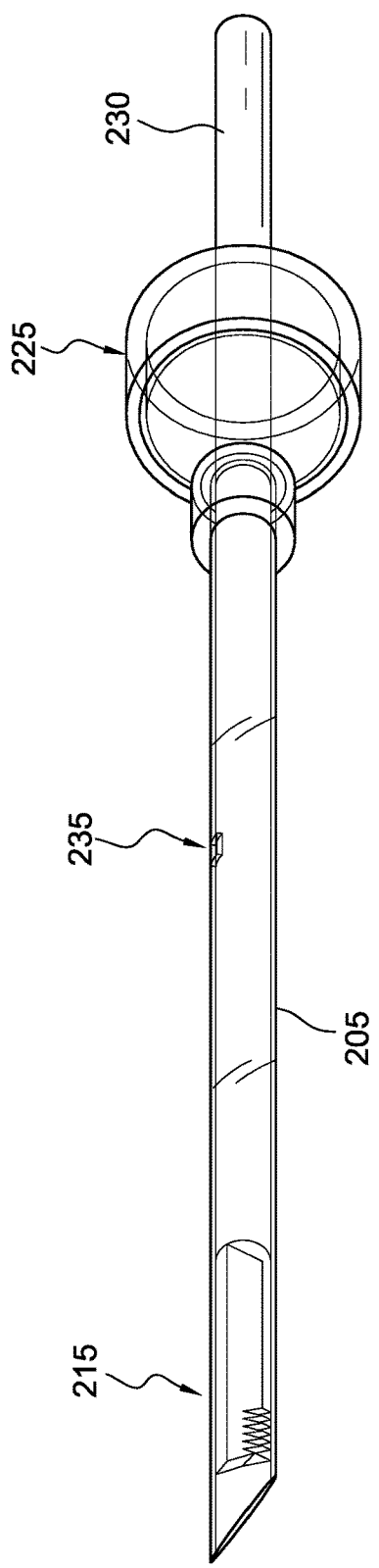
FIG. 2 shows a diagram illustrating further embodiments of the NK.

FIG. 2 shows an embodiment of the NK. The blade 215 is shown inside the needle 205. A connector mechanism 225 may connect the blade and needle to a control mechanism, which, as discussed with reference to FIG. 1, may be automated or may be controlled by hand by the doctor. Although the blade 215 is shown as serrated, in other embodiments, the blade may be flat-edged.

In the embodiment shown in FIG. 2, the blade 215 may be deployed out the front of the needle 205. The blade 215 may be connected to a shaft 230. The shaft 230 may slide through the needle 205 to deploy the blade 215. Once the blade 205 is outside the needle 205, the shaft 230 may oscillate to control motion of the blade, as, in an example embodiment, the blade oscillates to cut through the muscle. Once the muscle has been cut or once the procedure has been completed, the shaft 230 may be used to retract the blade 215 into the needle 205, and the needle 205 may be removed from the patient's body. The blade 215 in the 18 gauge needle 205 until the needle 205 is inserted into the tissue transcutaneously. The surgeon can activate the blade 215 which advances from the lumen of the needle (trocar) 205 and oscillates at desired (variable) frequencies and engages tissue to be cut. As such, the system has a sheathed blade 215 that is deployed from the sheath in an oscillating parallel motion perpendicular to the tissue that is intended to be cut. Once the tissue is cut, the surgeon stops the oscillation of the blade and the blade automatically retracts into the trocar. The trocar can then be removed without cutting additional tissue or skin.

In some embodiments, the shaft 230 may have a negative recess, and the needle 205 may have a corresponding tab, creating a lock mechanism 235. The lock mechanism 235 may ensure that the orientation of the blade 215 within the needle 205 is consistent. In one implementation, the tab may be pressed into the recess in the shaft 230, which may secure the orientation such that the blade 215 and shaft 230 may not rotate within the needle 205. In one embodiment, the tab in the needle 205 may slide into an elongated recess along the shaft 230, such that the tab may slide within the elongated recess as the blade 215 oscillates. This may ensure that the blade 215 does not rotate during oscillation. This may also ensure that the blade 215 does not oscillate beyond specified limits of deployment, as the tab may stop extension of the blade once it reaches the end of the elongated recess in the shaft.

Figure 3:
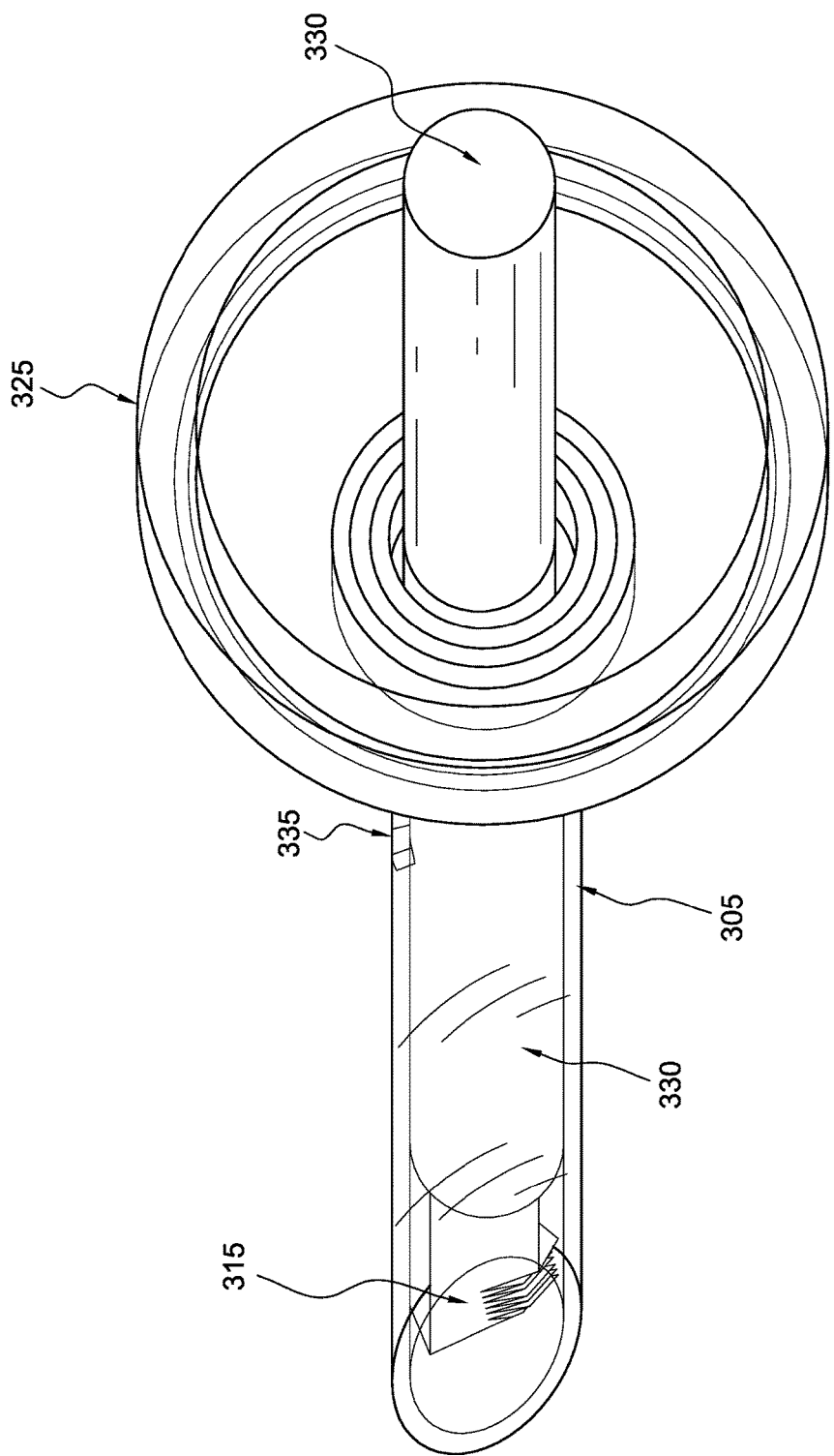
FIG. 3 shows a diagram illustrating further embodiments of the NK.

FIG. 3 shows an alternative view of one embodiment of the NK. The needle 305 may contain the blade 315 and shaft 330. In some embodiments, the NK may also have a lock mechanism 335. The shaft 330 may move through the connector mechanism 325 and the needle 305 to deploy and/or oscillate the blade 315.

Figure 4:
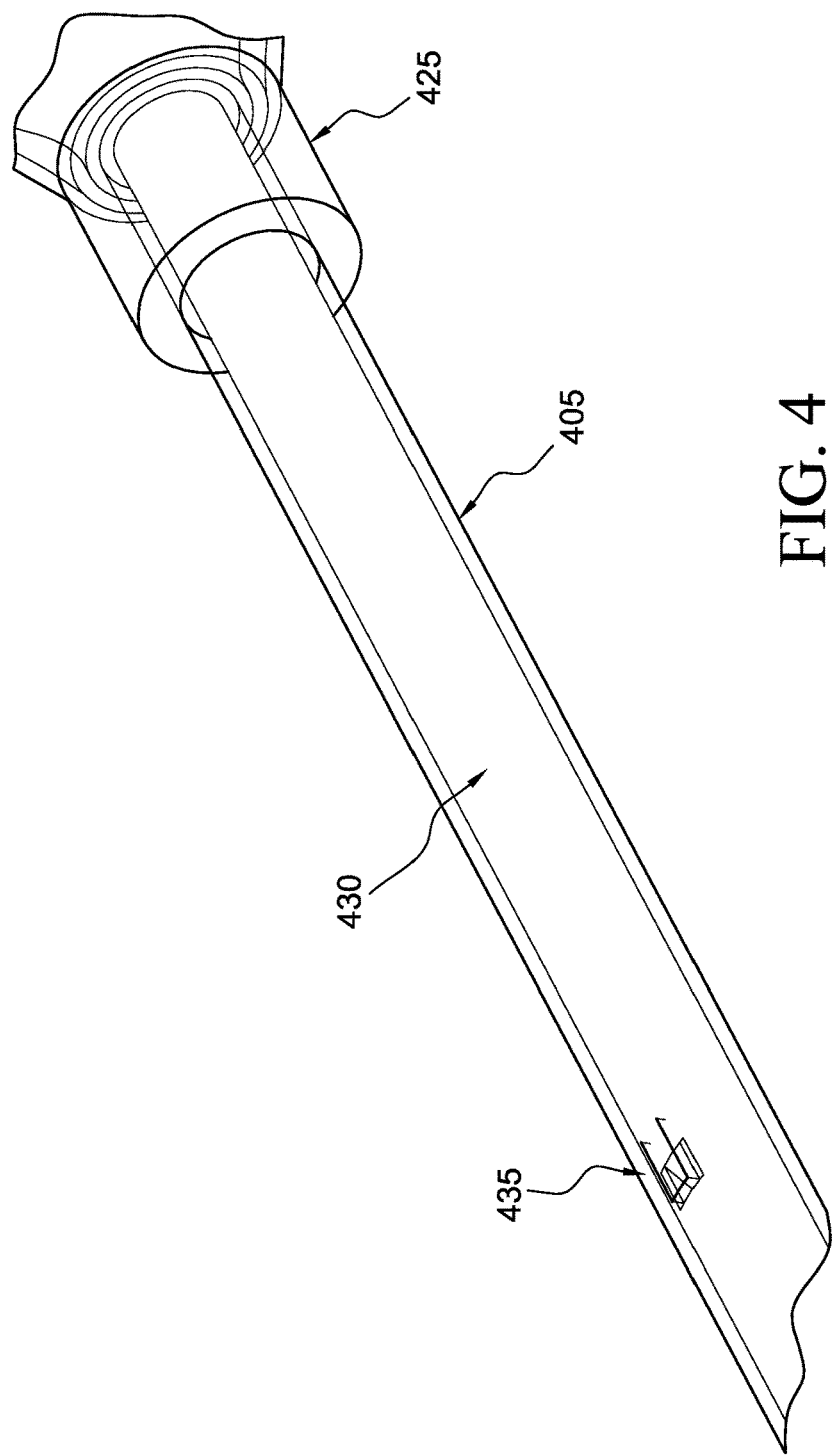
FIG. 4 shows a diagram illustrating further embodiments of the NK.

FIG. 4 illustrates an embodiment of the NK. The shaft 430 may be inside the needle 405, and the needle may be connected to the connector mechanism 425, while the shaft 430 may extend through the connector mechanism 425. The lock mechanism 435 may be provided with corresponding tabs and recesses in the needle 405 and shaft 430.

Figure 5:
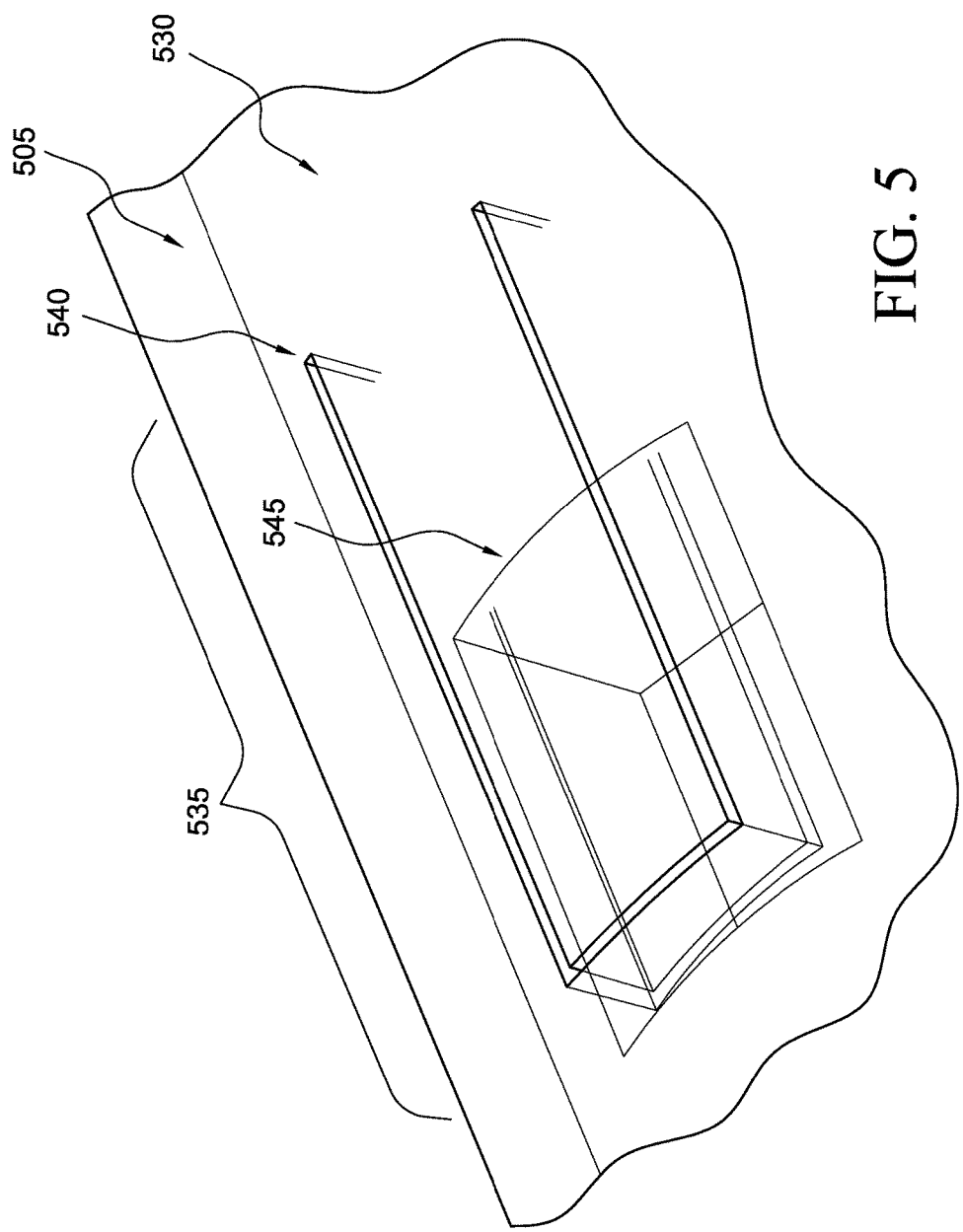
FIG. 5 shows a diagram illustrating further embodiments of the NK.

FIG. 5 illustrates a close-up embodiment of the NK. In the shown embodiment, the lock mechanism may comprise the tab 540 in the needle 505 and the recess 545 in the shaft 530. The tab 540 may be depressed into the recess 545. In depressing the tab, the shaft 530 may be locked into a particular orientation within the needle 505, such that the shaft cannot rotate within the needle. In some implementations, this may prevent the blade from rotating. In another embodiment, the depression 545 may be extended laterally along the shaft 530, such that the tab may slide within the elongated depression while the blade oscillates.

Figure 6:
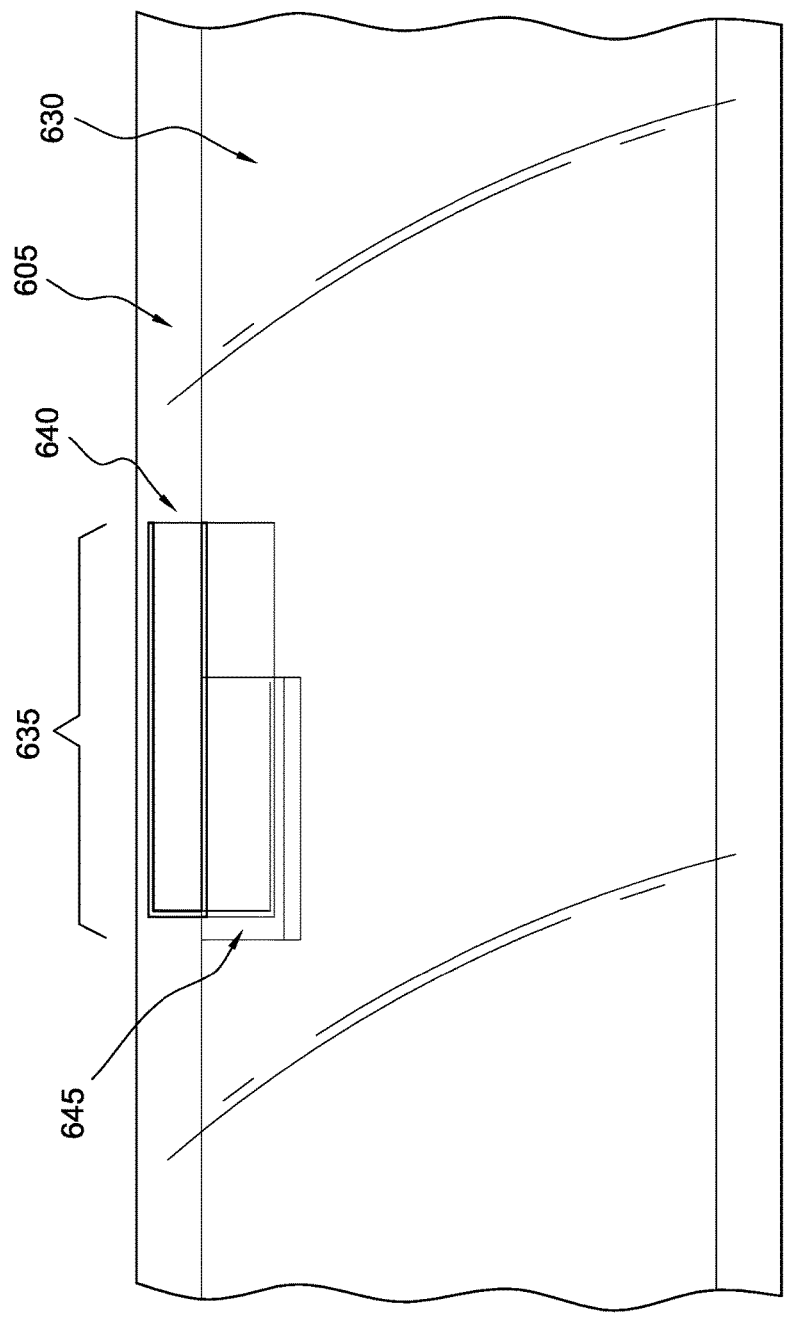
FIG. 6 shows a diagram illustrating further embodiments of the NK.

FIG. 6 illustrates another embodiment of the NK. A side view of the lock mechanism is shown, wherein the depression 645 in the shaft 630 and the tab 640 in the needle 605 may be engaged.

Figure 7:
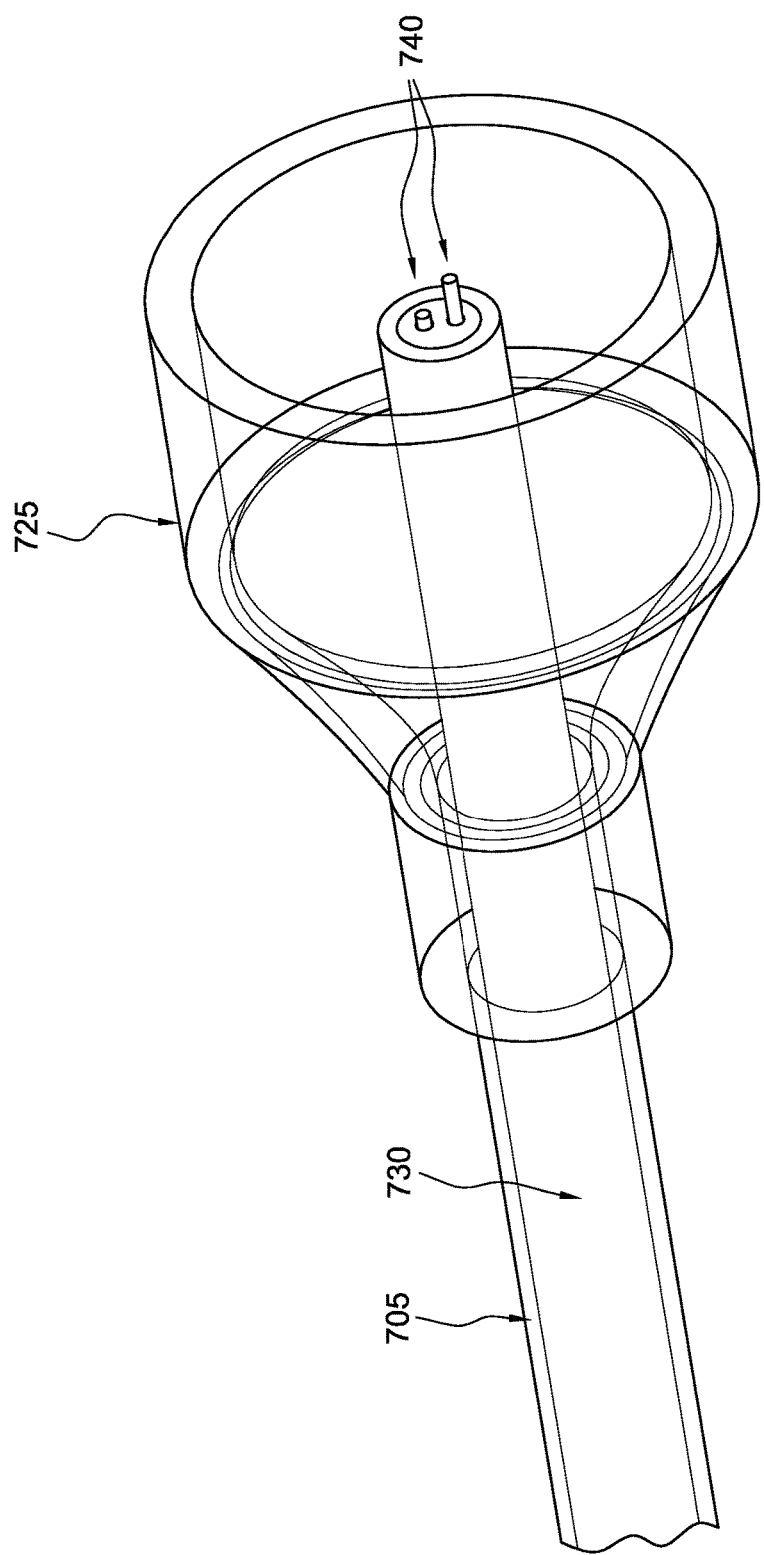
FIG. 7 shows a diagram illustrating further embodiments of the NK.

FIG. 7 shows another embodiment of the NK. The needle 705 may contain the shaft 730. The needle may connect to the connector mechanism 725, while the shaft 730 may extend through the connector mechanism. Pins 740 may be attached to the shaft 730. In some embodiments, the pins may be screws or other fasteners to connect the shaft 730 to a mechanism for moving the shaft to deploy and/or oscillate the blade.

In some embodiments, the mechanism for moving the shaft to deploy and/or oscillate the blade may be manual. In other embodiments, the mechanism for moving the shaft to deploy and/or oscillate may be motorized. In manual embodiments, the mechanism for moving the shaft may be connected to the shaft 730 by a tight fitting glue and/or glue-like substance. In motorized embodiments, the mechanism for moving the shaft may be connected to the shaft 730 via a collet system, whereby a series of fingers may crunch down on the shaft 730 with a tightening screw.

Figure 8:
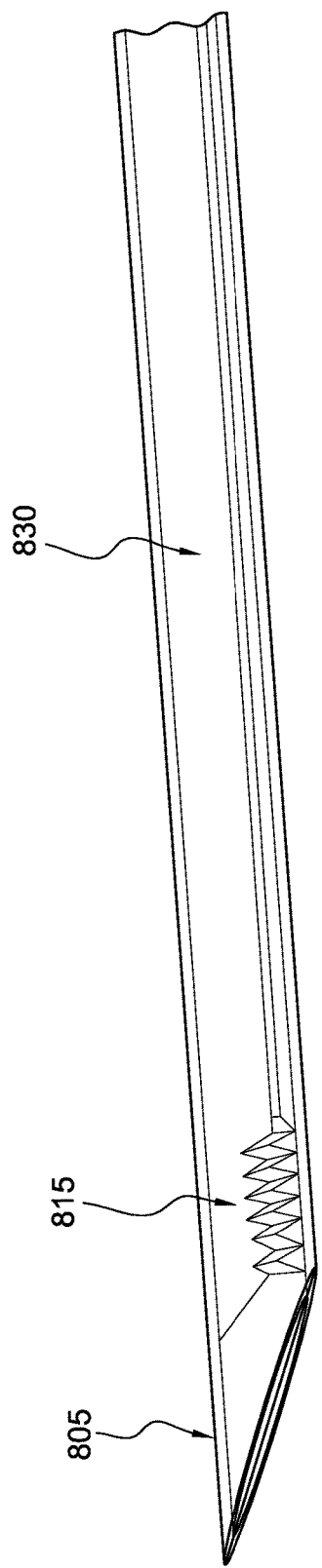
FIG. 8 shows a diagram illustrating further embodiments of the NK.
Figure 9:
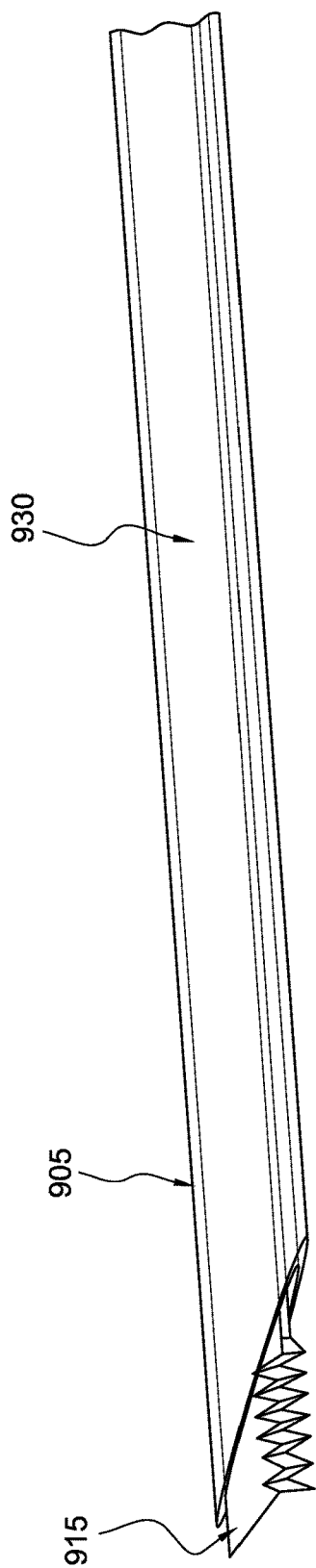
FIG. 9 shows a diagram illustrating further embodiments of the NK.
Figure 10:
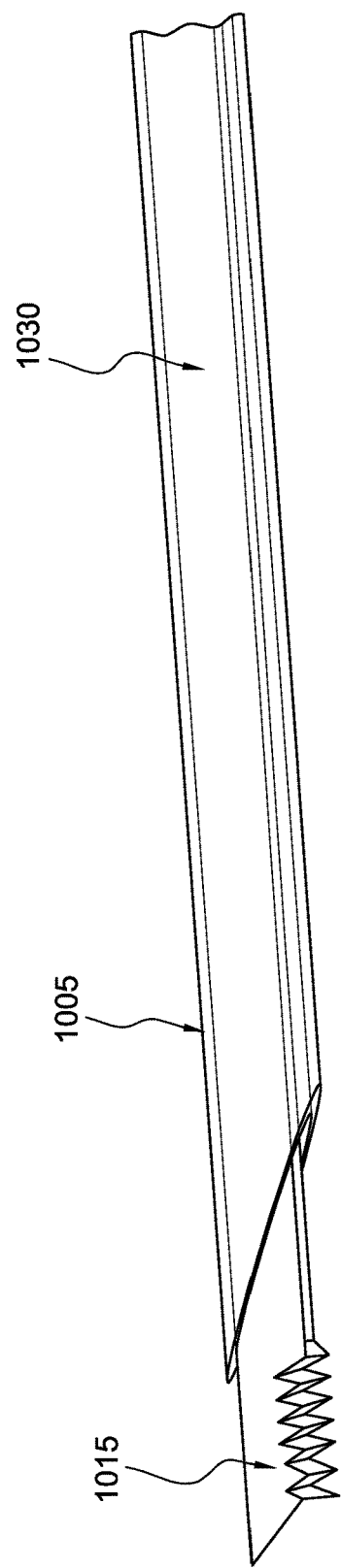
FIG. 10 shows a diagram illustrating further embodiments of the NK.

FIG. 8 shows an embodiment of the NK with a serrated blade. In one embodiment, the blade 815 may be serrated and the blade may begin within the needle 805. The blade 815 may be deployed to extend out the end of the needle 905, as shown in FIG. 9. FIG. 10 shows an embodiment of the NK were the blade may be fully deployed out the front of the needle.

Figure 11:
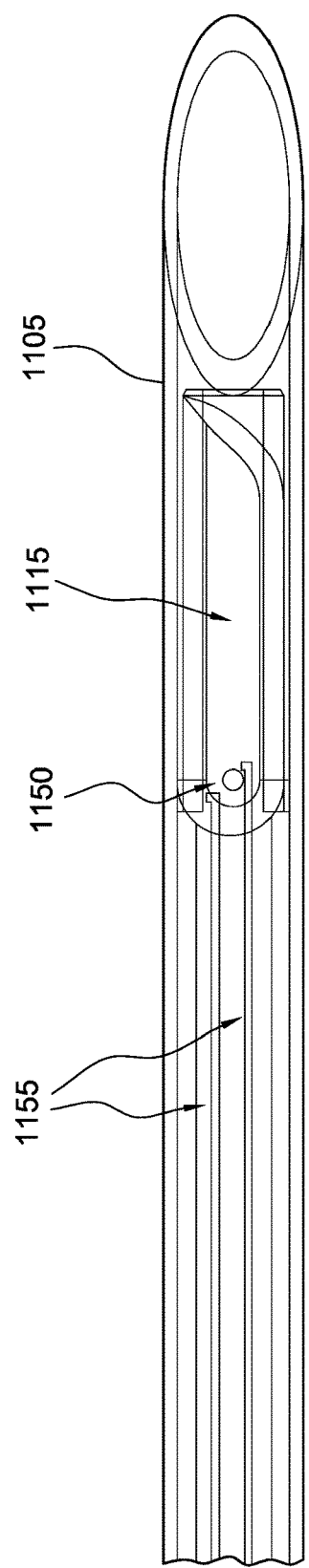
FIG. 11 shows a diagram illustrating further embodiments of the NK.

FIG. 11 shows an alternative embodiment of the NK. In this embodiment, the blade 1115 may deploy out the side of the needle 1105. The blade 1115 may be connected to a hinge 1150 around which the blade may rotate to deploy. In some implementations, there may be a split in the side of the needle 1105 to allow for deployment of the blade 1115. In one embodiment, the needle may be inserted into a patient prior to deployment of the blade.

In a side-deployment embodiment of the NK, the shaft may be replaced by two cables that may control deployment and/or oscillation of the blade. Applying tension to one of the cables may cause the blade 1115 to deploy out the side of the needle 1105. Applying tension to the other of the cables 1155 may cause the blade 1115 to retract back into the needle 1105.

Figure 12:
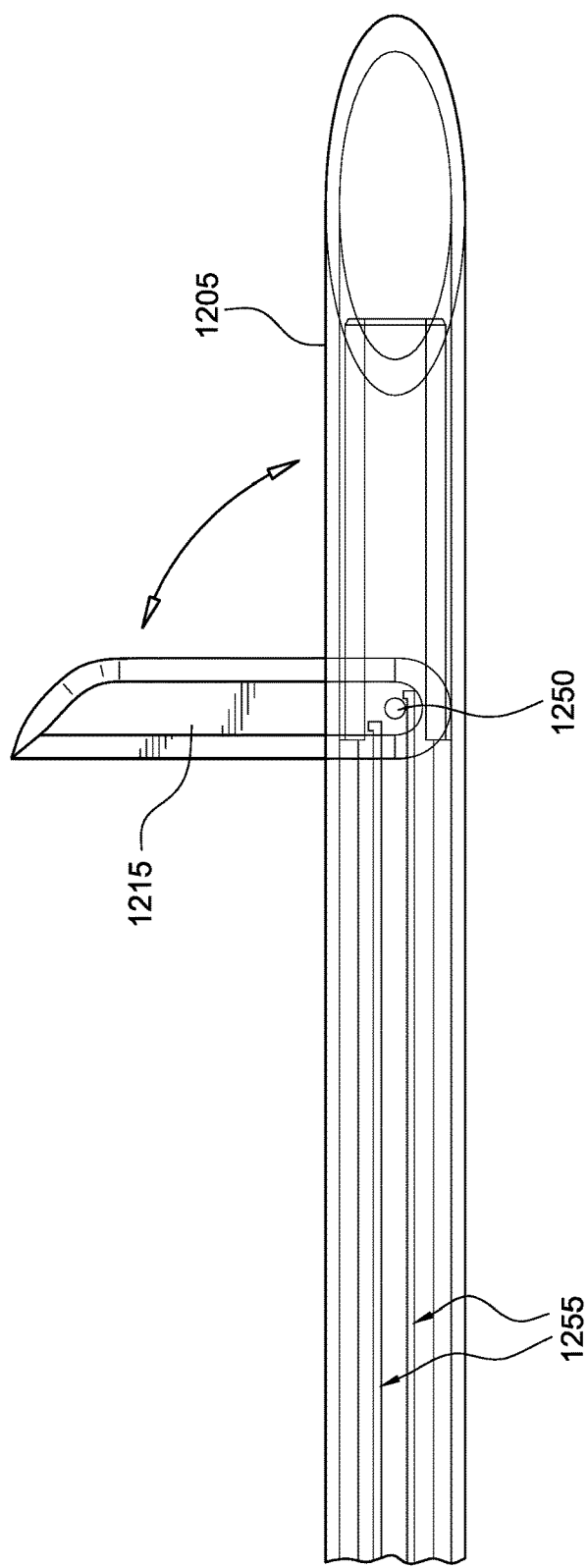
FIG. 12 shows a diagram illustrating further embodiments of the NK.

FIG. 12 shows an embodiment of the side-deployment implementation of the NK. The blade 1215 may rotate around the hinge 1250 and through the split in the side of the needle 1205, as shown by the arrow in FIG. 12. In some implementations, the blade 1215 may rotate back into the needle 1205. In some embodiments, the blade 1215 may oscillate between the deployed and retracted position. The oscillation may be caused by applying tension alternatively to each of the cables 1255.

FIG. 13 shows an alternative embodiment of the NK. The blade 1215 may deploy to an open position after entry into a patient and retract into a closed position before exit from the patient, and may remain deployed to oscillate along a portion of the length of the needle 1205. This oscillation is shown by the arrow in FIG. 13. In some embodiments, the blade 1315 may oscillate within the same split in the side of the needle 1305 through which the blade 1315 deploys. In alternative embodiments, the oscillation may extend through only a portion of the split. In yet another embodiment, the split may extend beyond the length of the blade 1315 to allow the blade 1315 to oscillate along a distance longer than the length of the blade 1315. In some embodiments, this oscillation may be provided by applying alternating tension and pressure on both of the cables 1355. The alternating tension and pressure may be applied manually or by a motor. Prior to removal of the needle 1305 from the patient, tension may be placed on one of the cables 1355 to rotate the blade around the hinge 1350 to retract the blade 1315 through the split and back into the needle 1305.

Figure 14A:
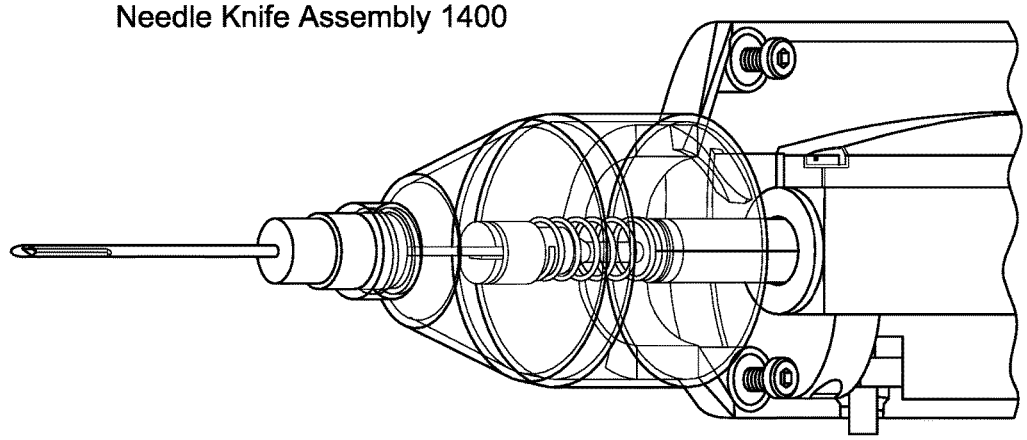
FIGS. 14*a-c* shows a diagram illustrating further embodiments of the NK, in FIG. 14*b* shows the blade in a neutral (sheathed) position
Figure 14B:
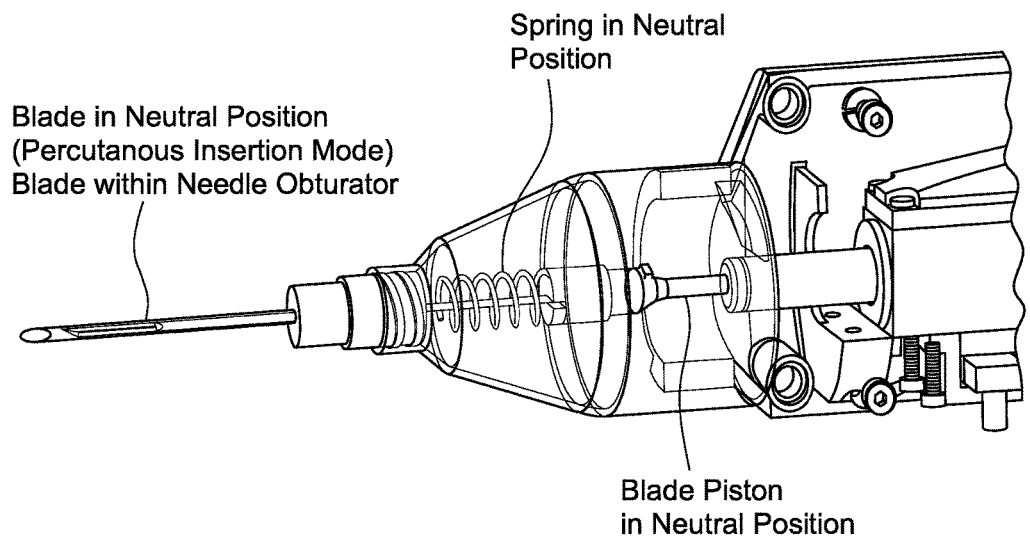
Figure 14C:
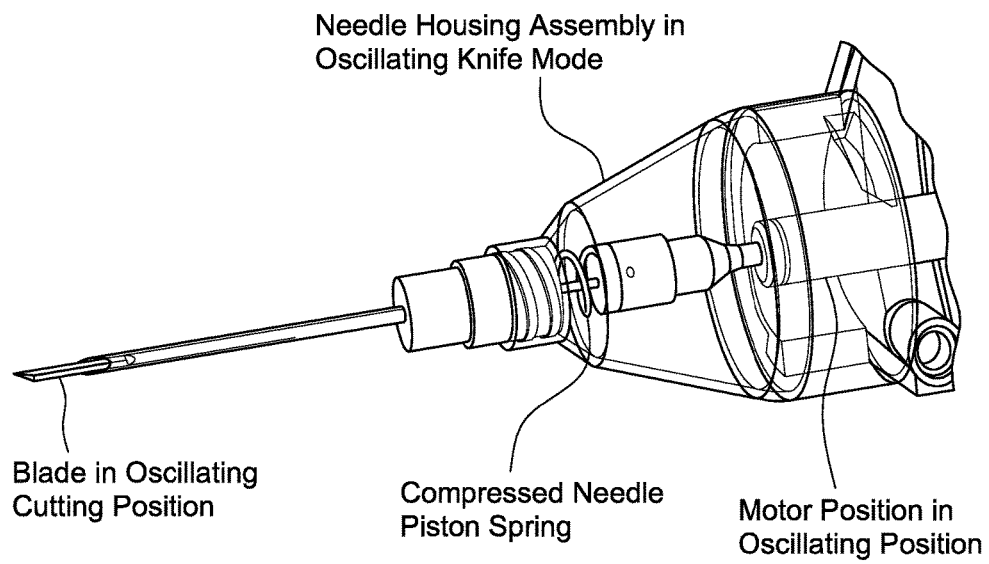

FIGS. 14*a-c* shows an alternative embodiment of the NK. FIG. 14*a* shows an assembled needle knife assembly 1400. As will be described in greater detail below, FIGS. 14*b-c* show the assembled needle knife assembly in various positions. FIG. 14*b* shows the blade in a neutral position (percutaneous insertion mode) with a blade disposed within a needle obturator, and a blade piston is disposed in a neutral position. FIG. 14*c* see shows the blade in an oscillating cutting position, such that a needle piston spring is compressed.

Figure 15A:
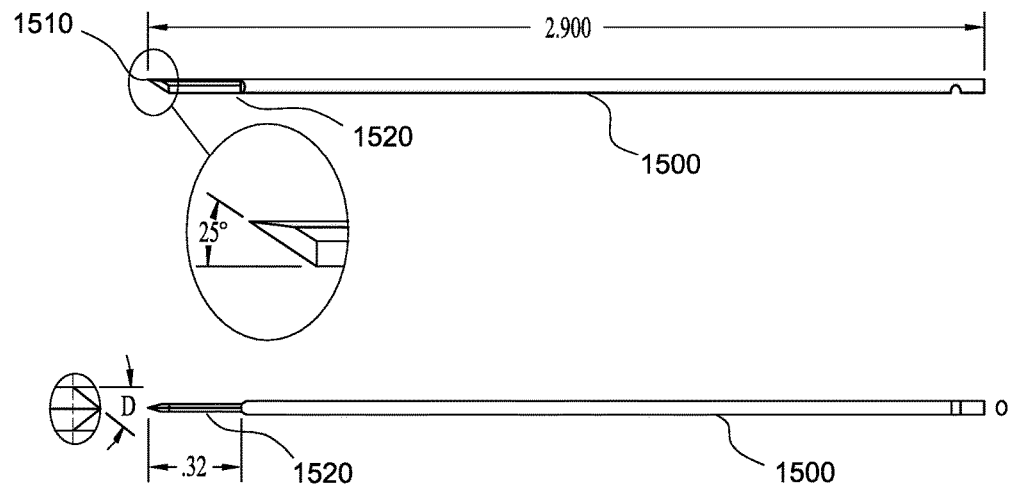
FIGS. 15*a-b* shows a diagram illustrating further embodiments of the NK having a non-serrated cutting blade.
Figure 15B:
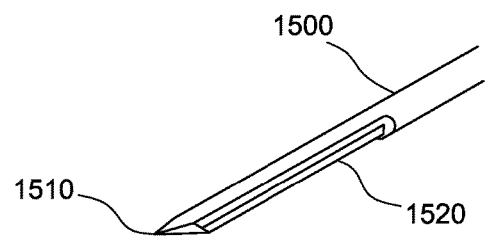
Figure 16A:
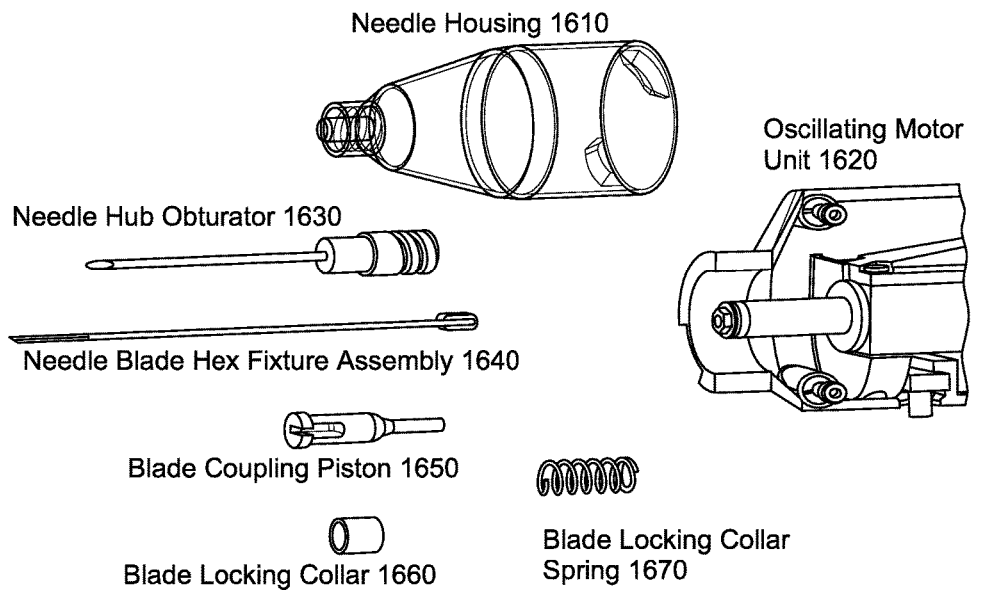
FIGS. 16*a-g* shows various diagrams illustrating a series of exploded and assembled views of yet another embodiment of the NK.
Figure 16B:
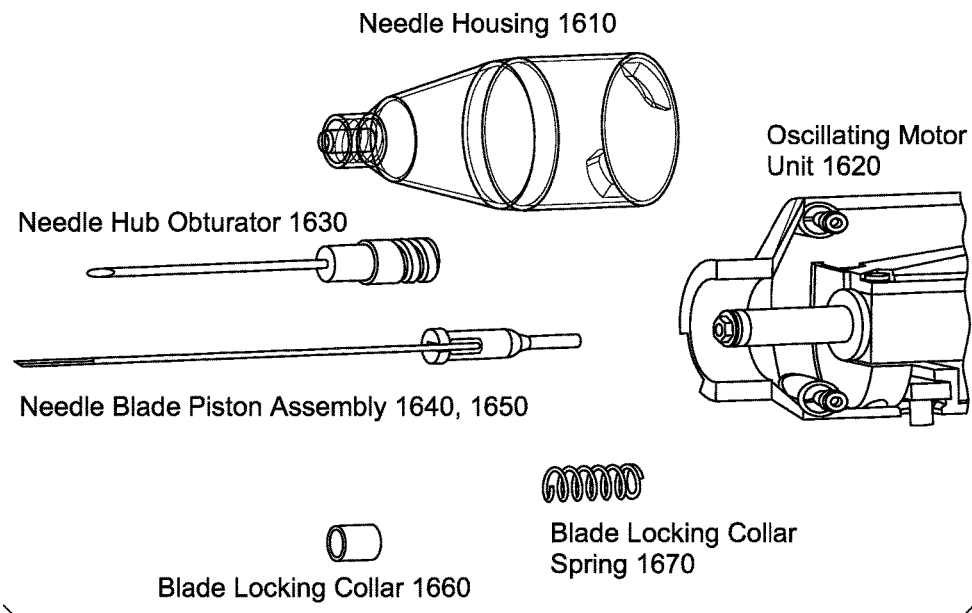
Figure 16C:
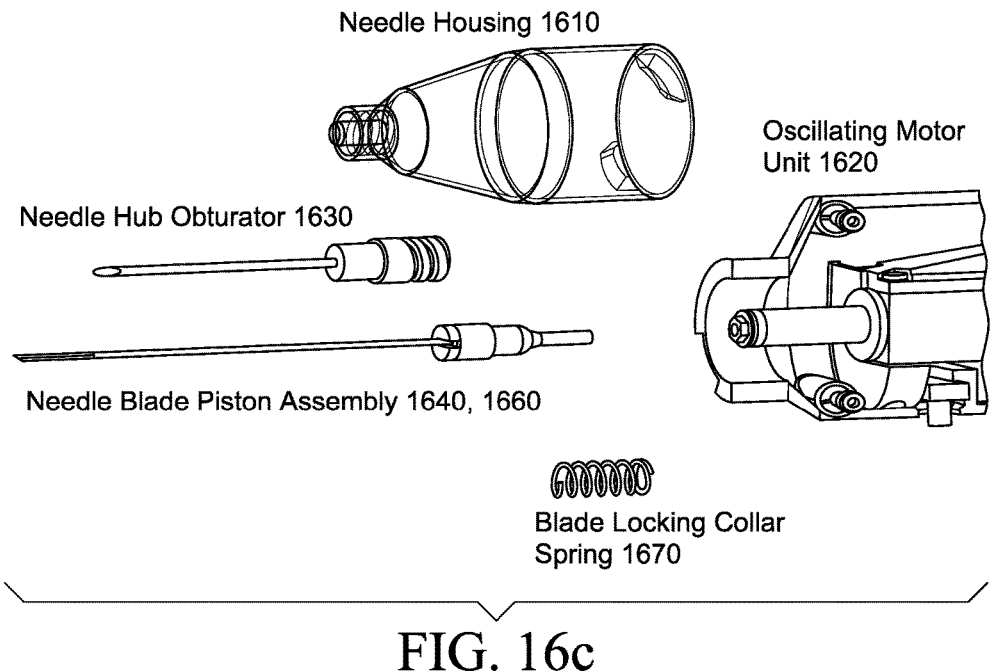
Figure 16D:
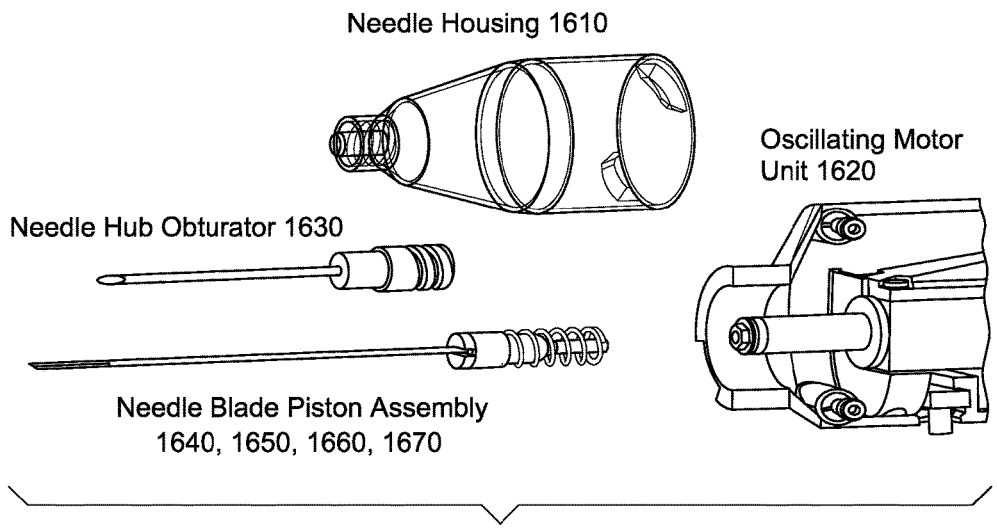
Figure 16E:
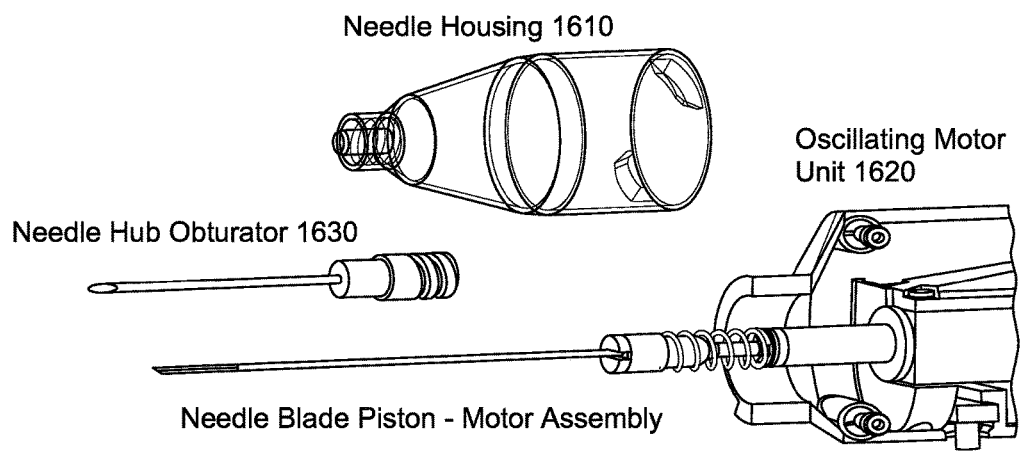
Figure 16F:
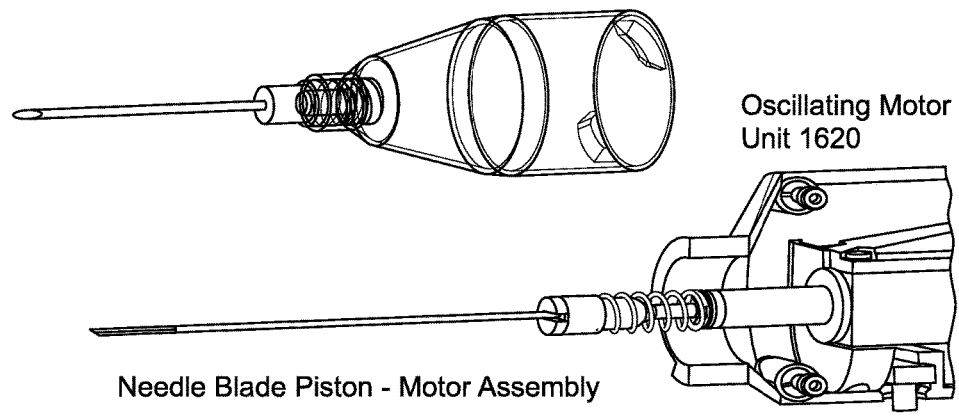
Figure 16G:
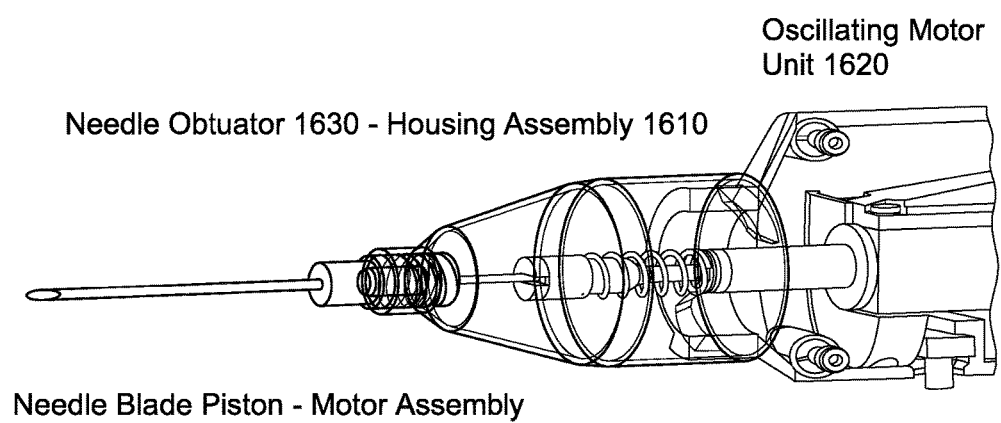
Figure 17A:
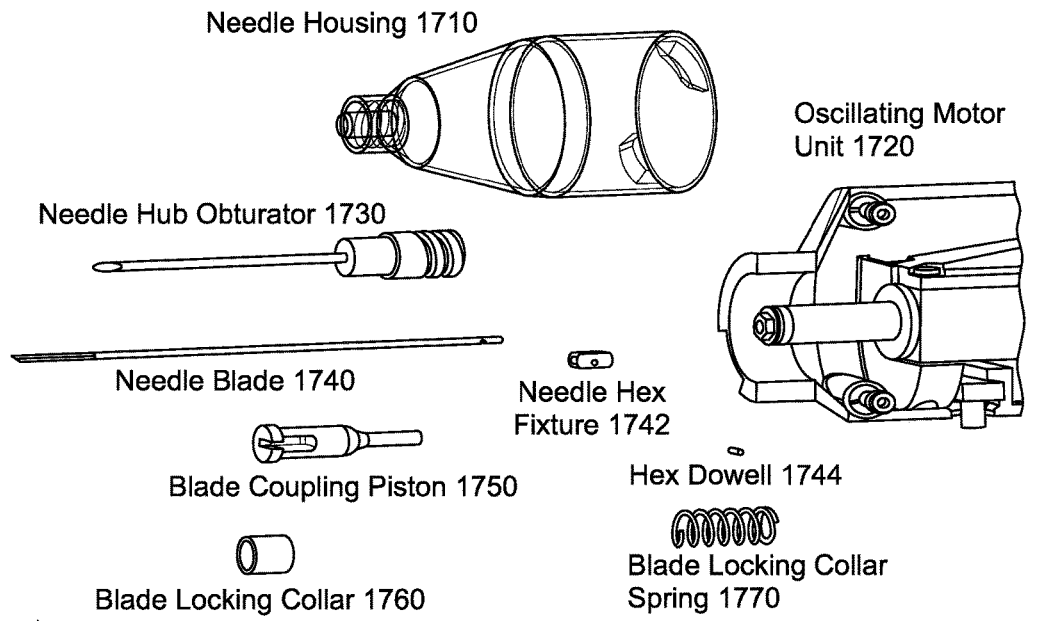
Figure 17B:
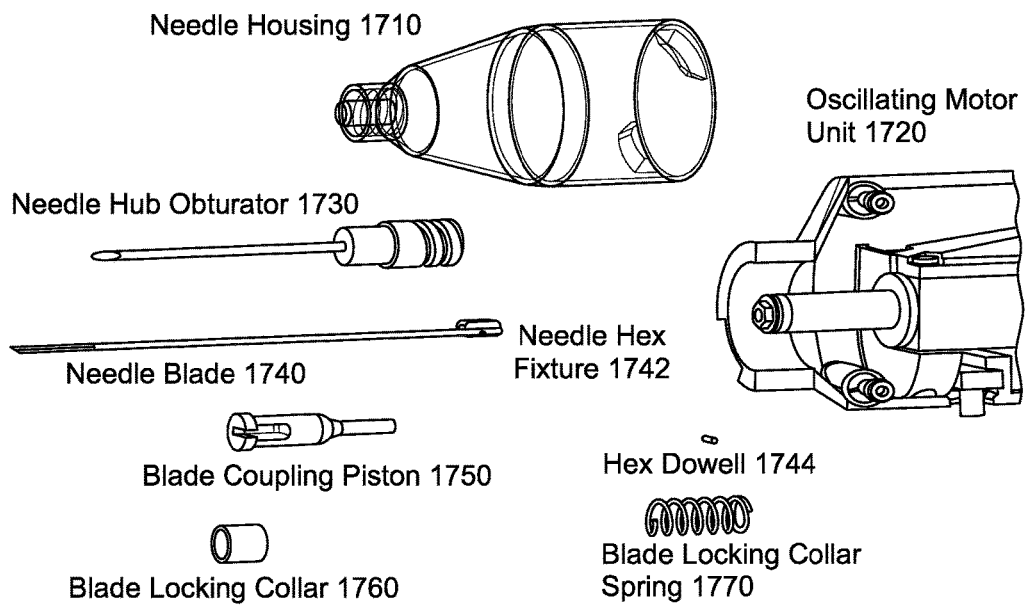
Figure 17C:
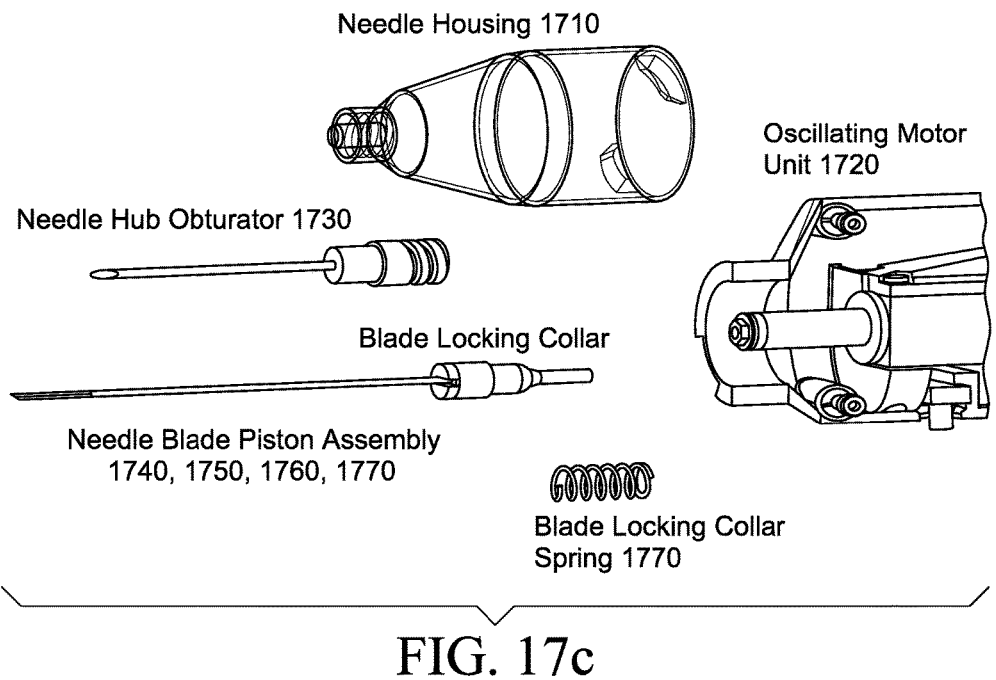
Figure 17D:
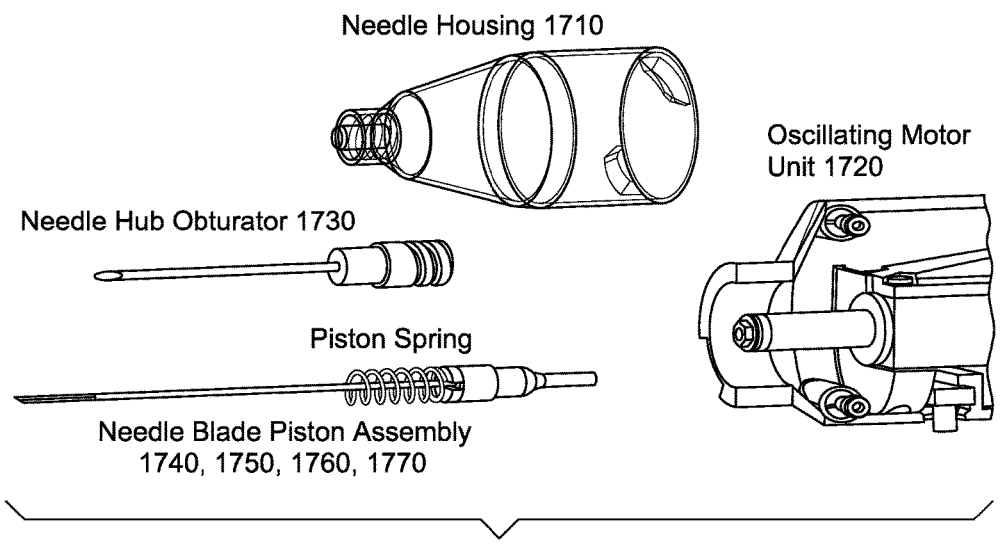
Figure 17E:
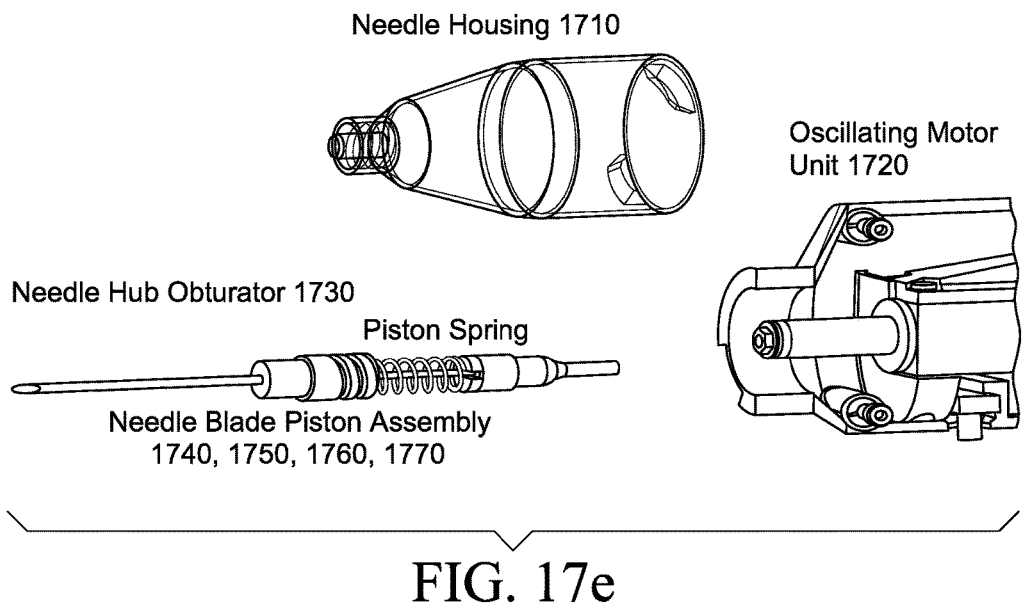
Figure 17F:
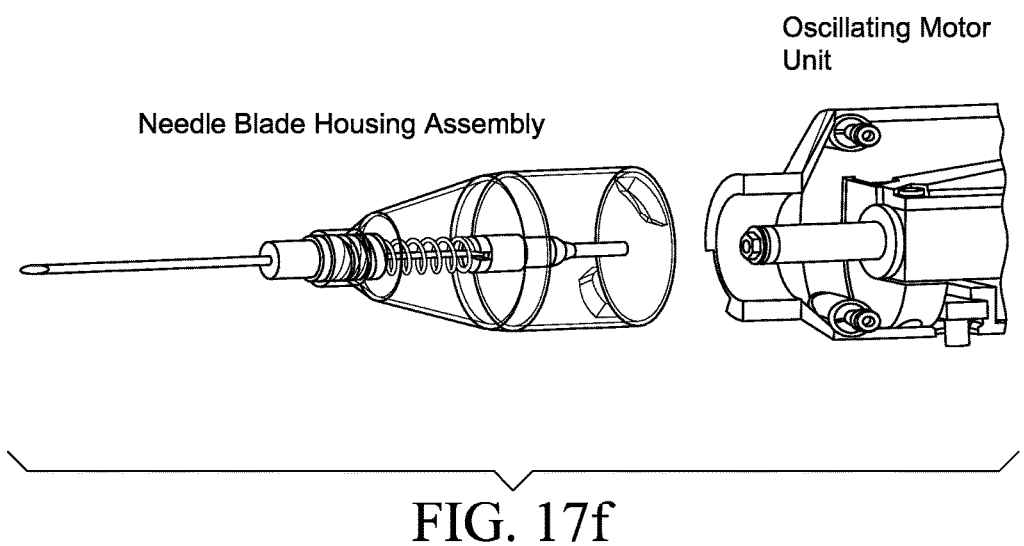

FIGS. 15*a-b* show an elongated needle blade 1500 having a sharpened tip 1510 and a cutting blade 1520. In this embodiment, the cutting blade 1520 is a non-serrated blade. In this embodiment, the cutting blade 1520 has a diameter which is less than or equal to the diameter of elongated needle blade 1500. In other embodiments, the cutting blade 1520 is serrated. In additional embodiments, the cutting blade 1520 has a diameter which is greater than the diameter of elongated needle blade 1500.

FIGS. 16*a-g* shows various diagrams illustrating a series of exploded and assembled views of an embodiment of the NK. In this embodiment, the needle housing 1610 is configured for connection to oscillating motor unit 1620. As shown, oscillating motor unit 1620 has had its cover removed to show components therewithin. Although various oscillating motor units maybe used, one such oscillating motor unit can be which can be used in Faulhaber Minimotor model LM1247-020-01, although other units may be used. In certain embodiments, the motor oscillates at 10 hertz. A needle hub obturator 1630 is configured for connection to needle housing 1610. The needle hub obturator 1630 has a trocar, cannula or lumen through which needle blade hex fixture assembly 1640 is disposed. The blade coupling piston 1650 is connected to needle blade text fixture assembly 1640 using a blade locking collar 1660. A blade locking collar spring 1670 is disposed to normally bias the blade in a neutral position (percutaneous insertion mode) such that the blade is normally maintained (or sheathed) within the needle obturator 1630, until oscillating motor unit 1620 is engaged. Upon engagement, the motor unit 1620 rapidly oscillates the needle blade 1640 to expose the knife portion of the needle blade, thereby cutting soft tissue in front of the needle knife and alongside the blade 1640.

FIGS. 17*a-h* shows various diagrams illustrating a series of exploded and assembled views of an embodiment of the NK. In this embodiment, the needle housing 1710 is configured for connection to oscillating motor unit 1720. As shown, oscillating motor unit 1720 has had its cover removed to show components therewithin. A needle hub obturator 1730 is configured for connection to needle housing 1710. The needle hub operator 1730 has a trocar, cannula or lumen through which a needle blade hex fixture assembly (1740, 1750, 1760, 1770) is disposed. Needle blade 1740 is connected to a needle hex fixture 1742 using a dowel 1744. The hex fixture 1742 fits within a blade coupling piston 1750 and is locked in place with a blade locking collar 1760. As such, the blade coupling piston 1750 is connected to needle blade text fixture assembly (1740, 1750, 1760, 1770) using this blade locking collar 1760. A blade locking collar spring 1770 is disposed to normally bias the blade in a neutral position (percutaneous insertion mode) such that the blade is normally maintained (or sheathed) within the needle obturator 1730, until oscillating motor unit 1720 is engaged. Upon engagement, the motor unit 1720 rapidly oscillates the needle blade 1740 to expose the knife portion of the needle blade, thereby cutting soft tissue in front of the needle knife and alongside the blade 1740.

As depicted in the figures, the embodiment of FIG. 16 differs from the embodiment of FIG. 17 in that the springs 1660, 1760 are disposed on different sides of the blade piston assembly. In each of these embodiments, the spring is used to bias said blade piston assembly to sheath the needle blade.

Figure 18:
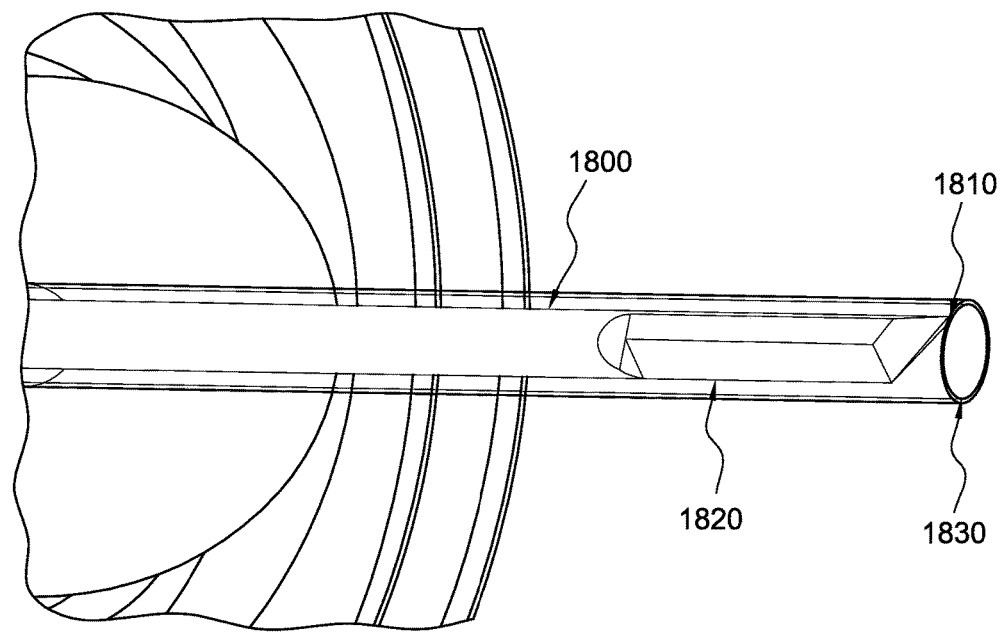
FIG. 18 shows the NK with the blade in the neutral (sheathed) position.

With reference to FIG. 18, elongated needle blade 1800 is shown as disposed within the trocar, obturator cannula or sheath 1830. The elongated needle blade 1800 has a leading tip 1810 and a cutting blade 1820. As shown, FIG. 18 depicts the needle knife assembly in which the elongated needle blade 1800 is fully disposed within the obturator 1830 during insertion into (and removal from) a patient. As such, this figure shows the NK in a neutral or fully sheathed position. In one embodiment, the leading tip 1810 is disposed within the obturator 1830 prior to engagement of the oscillating motor. In another embodiment, the leading tip 1810 is flush with the end of the obturator prior to engagement of the oscillating motor.

In another embodiment (not shown), the knife portion of the needle blade is replaced by a rotating cutting burr for use in cutting nasal cartilage and/or shaving bone. The needle knife may also be sued to treat cellulite and dermal scarring. In such an embodiment, a 16 gauge needle may be used to provide for an effective cutting burr element. The cutting burr is powered by a motorized unit connected to said needle housing.

In alternate embodiments, the needle trocar may be configured to receive a retractable laser or heating element (in lieu of a knife or blade) to cut soft tissue, cartilage or bone after insertion into the body. In such alternate embodiments, the needle assembly is configured to have electrical connectivity to the retractable laser or heating element. In another embodiment, the knife or blade may be configured to have a heating element disposed at or near the blade tip to assist in the cutting of soft tissue, cartilage or bone.

In order to address various issues and advance the art, the entirety of this application for NEEDLE KNIFE APPARATUSES, METHODS AND SYSTEMS (including the Cover Page, Title, Headings, Field, Background, Summary, Brief Description of the Drawings, Detailed Description, Claims, Abstract, Figures, Appendices, and otherwise) shows, by way of illustration, various embodiments in which the claimed innovations may be practiced. The advantages and features of the application are of a representative sample of embodiments only, and are not exhaustive and/or exclusive. They are presented only to assist in understanding and teach the claimed principles. It should be understood that they are not representative of all claimed innovations. As such, certain aspects of the disclosure have not been discussed herein. That alternate embodiments may not have been presented for a specific portion of the innovations or that further undescribed alternate embodiments may be available for a portion is not to be considered a disclaimer of those alternate embodiments. It will be appreciated that many of those undescribed embodiments incorporate the same principles of the innovations and others are equivalent. Thus, it is to be understood that other embodiments may be utilized and functional, logical, operational, organizational, structural and/or topological modifications may be made without departing from the scope and/or spirit of the disclosure. As such, all examples and/or embodiments are deemed to be non-limiting throughout this disclosure. Also, no inference should be drawn regarding those embodiments discussed herein relative to those not discussed herein other than it is as such for purposes of reducing space and repetition. For instance, it is to be understood that the logical and/or topological structure of any combination of any program components (a component collection), other components and/or any present feature sets as described in the figures and/or throughout are not limited to a fixed operating order and/or arrangement, but rather, any disclosed order is exemplary and all equivalents, regardless of order, are contemplated by the disclosure. Similarly, descriptions of embodiments disclosed throughout this disclosure, any reference to direction or orientation is merely intended for convenience of description and is not intended in any way to limit the scope of described embodiments. Relative terms such as "lower," "upper," "horizontal," "vertical," "above," "below," "up," "down," "top" and "bottom" as well as derivative thereof (e.g., "horizontally," "downwardly," "upwardly," etc.) should not be construed to limit embodiments, and instead, again, are offered for convenience of description of orientation. These relative descriptors are for convenience of description only and do not require that any embodiments be constructed or operated in a particular orientation unless explicitly indicated as such. Terms such as "attached," "affixed," "connected," "coupled," "interconnected," and similar may refer to a relationship wherein structures are secured or attached to one another either directly or indirectly through intervening structures, as well as both movable or rigid attachments or relationships, unless expressly described otherwise. Furthermore, it is to be understood that such features are not limited to serial execution, but rather, any number of threads, processes, services, servers, and/or the like that may execute asynchronously, concurrently, in parallel, simultaneously, synchronously, and/or the like are contemplated by the disclosure. As such, some of these features may be mutually contradictory, in that they cannot be simultaneously present in a single embodiment. Similarly, some features are applicable to one aspect of the innovations, and inapplicable to others. In addition, the disclosure includes other innovations not presently claimed. Applicant reserves all rights in those presently unclaimed innovations including the right to claim such innovations, file additional applications, continuations, continuations in part, divisions, and/or the like thereof. As such, it should be understood that advantages, embodiments, examples, functional, features, logical, operational, organizational, structural, topological, and/or other aspects of the disclosure are not to be considered limitations on the disclosure as defined by the claims or limitations on equivalents to the claims. While various embodiments and discussions of the NK have included discussions of home applications, however, it is to be understood that the embodiments described herein may be readily configured and/or customized for a wide variety of other applications and/or implementations.

What is claimed is:

1. A method of cutting soft tissue for eliminating forehead wrinkles, comprising:
    initially inserting a needle knife assembly transcutaneously into soft tissue within a forehead, wherein said soft tissue comprises muscle, said needle knife assembly including a needle obturator having a beveled point and a cutting blade disposed within said needle obturator for cutting said muscle, said cutting blade being sheathed within said obturator during the initial transcutaneous insertion of the needle knife assembly into the forehead; and
    actuating a motor to rapidly oscillate said needle knife assembly between a retracted position and an extended position to cut said muscle within the forehead using said cutting blade, wherein said cutting blade wherein said cutting blade is disposed outside said needle obturator as the needle knife moves to and from said extended position.

2. A method of cutting muscle within a forehead to eliminate wrinkles, comprising:
    initially inserting a needle knife assembly transcutaneously into tissue within the forehead, said needle knife assembly including a needle having a beveled point and a cutting blade disposed within said needle for cutting the muscle within the forehead, said cutting blade being sheathed within said needle during the initial insertion of the needle knife assembly into the forehead; and
    actuating a motor to rapidly oscillate said cutting blade between a retracted position and an extended position to cut the muscle using said cutting blade, wherein said cutting blade is disposed outside said needle as the cutting blade moves to and from said extended position.

3. The method of claim 2, further comprising removing the needle knife assembly from the forehead after the muscle is cut.

4. The method of claim 2, further comprising incorporating an imaging technique to track a location of the needle knife after it has been transcutaneously inserted into the tissue within the forehead.

5. A method of cutting soft tissue under skin of a forehead of a patient to eliminate forehead wrinkles comprising:
    providing a needle knife device including a needle having a beveled point and a lumen and a blade that is capable of being oscillated within the lumen between a retracted position where the blade is disposed within the needle and a deployed position where the blade is disposed outside the needle;

inserting a leading portion of the needle into the skin of the patient and to an area of the forehead having muscle responsible for wrinkle creation while the blade is in a retracted position; and deploying the blade out of the leading portion of the needle such that the blade cuts through the muscle thereby eliminating forehead wrinkles.

6. The method of claim 5, wherein after deploying the blade out of the leading portion of the needle the blade is then retracted back into the leading portion of the needle and then re-deployed thereby oscillating the blade to cut the muscle responsible for wrinkle creation.

7. The method of claim 6, further comprising retracting the blade back into the leading portion of the needle after the muscle has been cut.

8. The method of claim 7, further comprising removing the leading portion of the needle knife along with the retracted blade from insertion under the skin of the patient.

9. The method of claim 5, wherein deploying the blade out of the leading portion of the needle includes deploying the blade substantially perpendicular to the muscle to be cut.

10. A method of cutting soft tissue under facial skin of a patient to eliminate crow's feet wrinkles comprising:

providing a needle knife device including a needle having a beveled point and a lumen and a blade that is capable of being oscillated within the lumen between a retracted position where the blade is disposed within the needle and a deployed position where the blade is disposed outside the needle;

inserting a leading portion of the needle into the facial skin of the patient and to an area having muscle responsible for crow's feet wrinkle creation while the blade is in a retracted position; and deploying the blade out of the leading portion of the needle such that the blade cuts through the muscle thereby eliminating crow's feet wrinkles.

11. The method of claim 10, further comprising removing the leading portion of the needle knife along with the retracted blade from insertion under the facial skin of the patient.

12. A method of cutting soft tissue under facial skin of a patient comprising:

providing a needle knife device including a needle having a beveled point and a lumen and a blade that is capable of being oscillated within the lumen between a retracted position where the blade is disposed within the needle and a deployed position where the blade is disposed outside the needle;

inserting a leading portion of the needle into the facial skin of the patient and to an area having muscle while the blade is in a retracted position; and deploying the blade out of the leading portion of the needle such that the blade cuts through the muscle.

13. The method of claim 12, further comprising removing the leading portion of the needle knife along with the retracted blade from insertion under the facial skin.

* * * * *